United States Patent
Bischoff et al.

(10) Patent No.: US 8,430,852 B2
(45) Date of Patent: Apr. 30, 2013

(54) THERAPEUTIC SLEEVE FOR IMPLANTABLE MEDICAL DEVICE

(75) Inventors: Thomas C. Bischoff, Minneapolis, MN (US); Robyn L. Jagler, Eagan, MN (US)

(73) Assignee: Medtronic, Inc., Minneapolis, MN (US)

( * ) Notice: Subject to any disclaimer, the term of this patent is extended or adjusted under 35 U.S.C. 154(b) by 112 days.

(21) Appl. No.: 12/415,311

(22) Filed: Mar. 31, 2009

(65) Prior Publication Data
US 2009/0198197 A1 Aug. 6, 2009

Related U.S. Application Data

(63) Continuation-in-part of application No. 12/104,932, filed on Apr. 17, 2008, now Pat. No. 7,947, 301.

(60) Provisional application No. 60/912,234, filed on Apr. 17, 2007.

(51) Int. Cl.
 *A61M 5/32* (2006.01)
(52) U.S. Cl.
 USPC .......................................... 604/265; 606/174
(58) Field of Classification Search ................... 604/523, 604/524, 530, 265
See application file for complete search history.

(56) References Cited

U.S. PATENT DOCUMENTS

| | | | |
|---|---|---|---|
| 4,122,858 A | 10/1978 | Schiff | |
| 4,230,110 A | 10/1980 | Beroff | |
| 4,278,092 A | 7/1981 | Borsanyi | |
| 4,632,670 A | 12/1986 | Mueller, Jr. | |
| 4,676,782 A | 6/1987 | Yamamoto | |
| 4,821,716 A | 4/1989 | Ghajar | |
| 4,897,082 A | 1/1990 | Erskine | |
| 5,053,015 A | 10/1991 | Gross | |
| 5,129,891 A | 7/1992 | Young | |
| 5,217,493 A * | 6/1993 | Raad et al. ................. | 623/11.11 |
| 5,226,898 A | 7/1993 | Gross | |
| 5,356,381 A | 10/1994 | Ensminger | |
| 5,364,340 A | 11/1994 | Coll | |
| 5,391,156 A | 2/1995 | Hildwein | |
| 5,713,858 A | 2/1998 | Heruth | |
| 5,746,722 A | 5/1998 | Pohndorf | |
| 5,792,115 A | 8/1998 | Horn | |
| 5,820,607 A | 10/1998 | Tcholakian | |

(Continued)

FOREIGN PATENT DOCUMENTS

| | | |
|---|---|---|
| DE | 10015323 | 11/2000 |
| EP | 0 865 799 | 9/1998 |
| WO | WO 03/090820 | 11/2003 |
| WO | WO 2008/088982 | 7/2008 |

OTHER PUBLICATIONS

U.S. Appl. No. 12/056,547, filed Mar. 27, 2008, Sage.

(Continued)

*Primary Examiner* — Tatyana Zalukaeva
*Assistant Examiner* — Brandy C Scott

(57) ABSTRACT

A therapeutic sleeve is disposable about a therapy delivery element. The sleeve has a first opening, a second opening, and a radially elastic body member disposed between the first and second opening. The body member forms a lumen extending from the first opening to the second opening and is configured to be disposed about the therapy delivery element. The sleeve further includes a therapeutic agent releasable from the body member when implanted in a patient.

19 Claims, 13 Drawing Sheets

U.S. PATENT DOCUMENTS

| | | | |
|---|---|---|---|
| 5,843,146 | A | 12/1998 | Cross, Jr. |
| 5,902,283 | A | 5/1999 | Darouiche |
| 6,395,017 | B1 | 5/2002 | Dwyer |
| 6,428,557 | B1 | 8/2002 | Hilaire |
| 6,447,533 | B1 | 9/2002 | Adams |
| 6,451,003 | B1 | 9/2002 | Prosl |
| 6,528,107 | B2 | 3/2003 | Chinn et al. |
| 6,554,802 | B1 | 4/2003 | Pearson |
| 6,743,209 | B2 | 6/2004 | Brown |
| 6,843,784 | B2 | 1/2005 | Modak |
| 6,997,919 | B2 | 2/2006 | Olsen |
| 7,090,661 | B2 | 8/2006 | Morris |
| 7,594,911 | B2 | 9/2009 | Power |
| 2003/0199853 | A1 | 10/2003 | Olsen |
| 2005/0101915 | A1 | 5/2005 | Morris |
| 2005/0107744 | A1 | 5/2005 | Morris |
| 2005/0147643 | A1* | 7/2005 | Hunter et al. .............. 424/423 |
| 2005/0209583 | A1* | 9/2005 | Powers et al. .............. 604/533 |
| 2005/0267543 | A1 | 12/2005 | Heruth |
| 2006/0009806 | A1 | 1/2006 | Heruth |
| 2006/0039946 | A1* | 2/2006 | Heruth et al. .............. 424/422 |
| 2006/0051392 | A1 | 3/2006 | Heruth |
| 2006/0051393 | A1 | 3/2006 | Heruth |
| 2006/0084940 | A1 | 4/2006 | Olsen |
| 2006/0084941 | A1 | 4/2006 | Olsen |
| 2006/0195066 | A1 | 8/2006 | Cross, Jr. |
| 2007/0196423 | A1* | 8/2007 | Ruane et al. .............. 424/423 |
| 2008/0275401 | A1 | 11/2008 | Sage |
| 2009/0248054 | A1* | 10/2009 | Sage et al. .............. 606/174 |

OTHER PUBLICATIONS

International Preliminary Report on Patentability and Written Opinin for PCT/US2009/038269.

International Search Report for PCT/US2009/038269.

Office Action issued Apr. 23, 2012, U.S. Appl. No. 13/083,983.

* cited by examiner

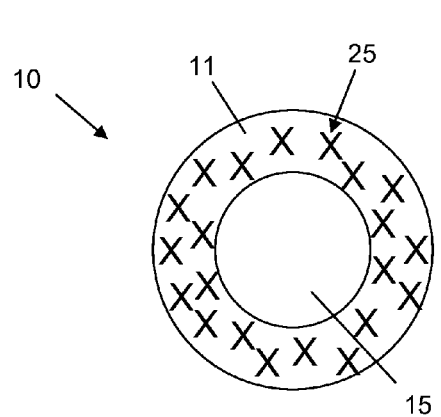
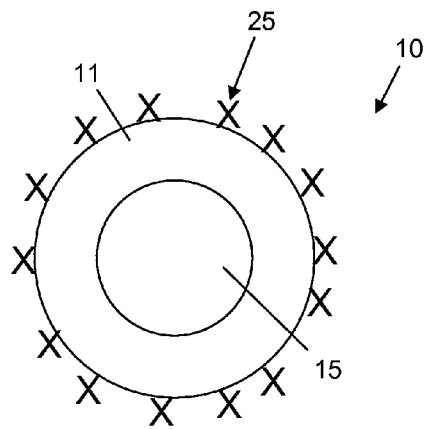
FIG. 3A    FIG. 3B
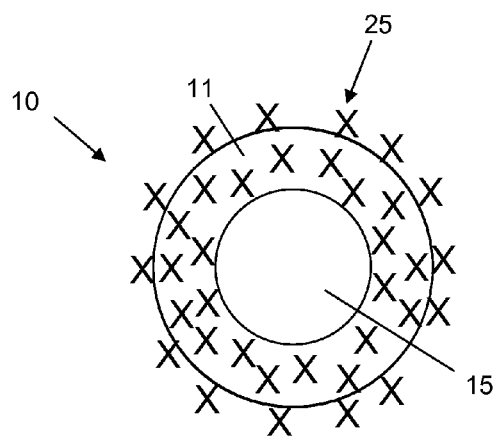
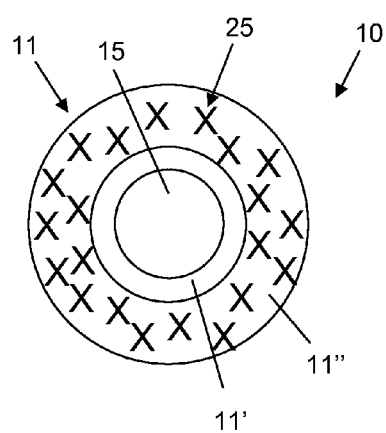
FIG. 3C    FIG. 3D

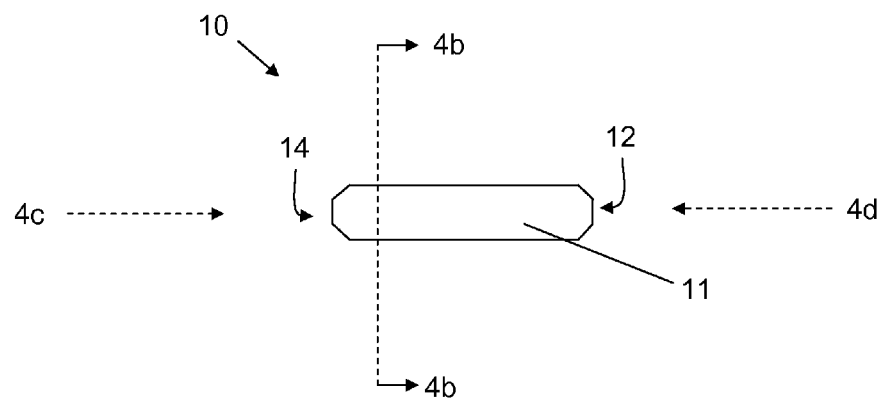
FIG. 4A
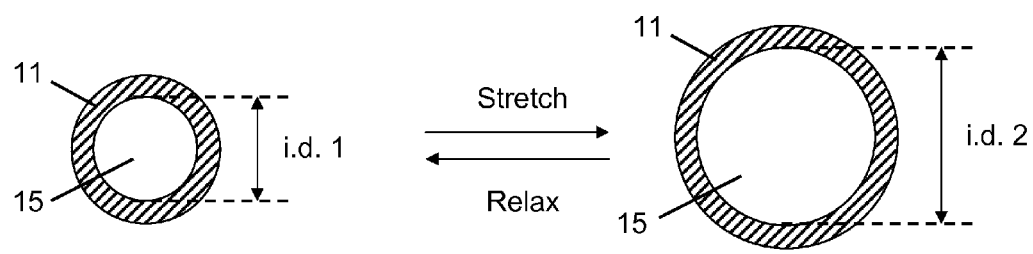
FIG. 4B
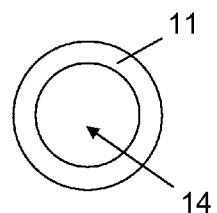 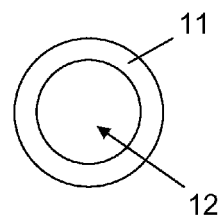
FIG. 4C  FIG. 4D

FIG. 5D                    FIG. 5E

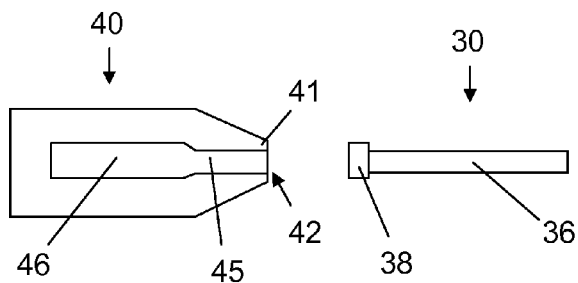
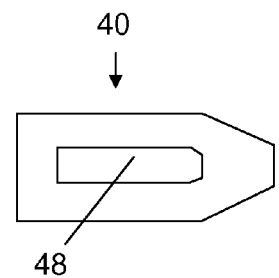
FIG. 7C　　　　　　　　　　FIG. 7D
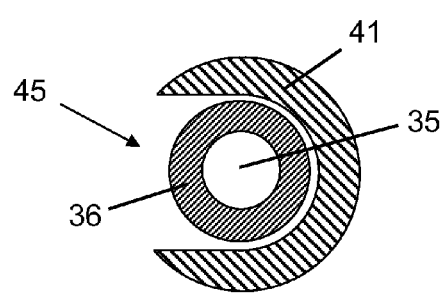
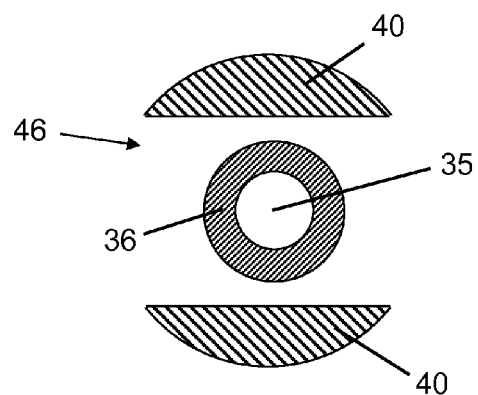
FIG. 7E　　　　　　　　　　FIG. 7F
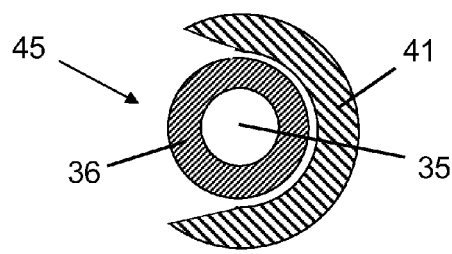
FIG. 7G

THERAPEUTIC SLEEVE FOR IMPLANTABLE MEDICAL DEVICE

RELATED APPLICATION

This application is a Continuation-In-Part application of (i) application Ser. No. 12/104,932, filed on Apr. 17, 2008 and published on Oct. 23, 2008 as US 2008/0260796, which claims the benefit of Provisional Application No. 60/912,234, filed on Apr. 17, 2007, which applications are hereby incorporated herein by reference in their entireties.

FIELD

This disclosure relates, inter alia, to implantable medical devices. More particularly, it relates to systems, methods and devices for delivering a therapeutic substance from a sleeve associated with an implantable medical device.

BACKGROUND

Implantation of medical devices, such as pacemakers, neurostimulators, implanted drug pumps, leads, catheters, etc, has been associated with adverse consequences, such as formation of scar tissue surrounding the implant and infection due to bacteria introduced during implantation. Attempts to prevent or control such adverse reactions have included administration of drugs, completely separate from the intended primary therapy of the implanted medical device. In some cases, systemically administered drugs, e.g. orally, intravenously, or intramuscularly administered drugs, have proven effective in treating complications due to medical device implantation. In other cases, systemic delivery has been ineffective due to, e.g., pharmacokinetic or pharmacodynamic characteristics of the drug, the location of the implanted device, or side effects of the drug. To increase effectiveness in these situations, some implanted devices have been modified to elute the drug into the surrounding tissues.

One common way of providing local drug elution is to dispose a polymer layer on the implantable medical device and embed the drug into the polymer during manufacturing. When hydrated after implant, the drug diffuses out of the polymer into surrounding tissue. Various methods of impregnating polymers with drugs have been used, including mixing the drug into the melted polymer prior to processing (e.g. molding or extrusion), and diffusing the drug into a finished polymer component using chemicals to swell the polymer for rapid loading. In some cases, the implantable medical device (IMD) is made from a polymer that is compatible with the drug, and the drug can be loaded directly into the device.

However, incorporation of a therapeutic agent into or onto polymeric material of an implantable medical device may have several drawbacks. For example, the therapeutic agent may not be compatible with sterilization techniques typically employed with medical device.

SUMMARY

The present disclosure describes, inter alia, accessory implantable medical devices that contain an elutable therapeutic agent and that are configured to be disposed about and snuggly engage an implantable therapy delivery element, such as a lead or catheter.

In various embodiments, this disclosure describes a therapeutic sleeve that is disposable about a therapy delivery element. The sleeve has a first opening, a second opening, and a radially elastic body member disposed between the first and second opening. The body member forms a lumen extending from the first opening to the second opening and is configured to be disposed about the therapy delivery element. The sleeve further includes a therapeutic agent releasable from the body member when implanted in a patient. At least a portion of the body member has a first inner diameter defined by the lumen in a relaxed state and a second inner diameter defined by the lumen in a radially stretched state. The first inner diameter is smaller than the second inner diameter and is smaller than the outer diameter of the therapy delivery element. The second inner diameter is larger than the outer diameter of the therapy delivery element. When placed about a therapy delivery element, the sleeve grippingly engages the therapy delivery element. In some embodiments, the sleeve may be disposed loosely about the device.

In various embodiments, the disclosure describes kits and systems that include a therapeutic agent-containing sleeve and methods associated with the sleeve.

By providing accessory therapeutic agent-containing devices, the accessory device can be sterilized separately from the therapy delivery element, which may be helpful in situations where the therapeutic agent is not compatible with a sterilization process to which the therapy delivery element may be subjected. In addition, by incorporating the therapeutic agent into the accessory device, rather than the therapy deliver element, the therapeutic agent is less likely to compromise the structural integrity or adversely affect desired properties of the therapy delivery agent. Further, the accessory device allows a health care provider to make a determination as to whether to include the therapeutic agent-containing device in the implant procedure. Moreover, an accessory device may be packaged separately from the therapy delivery element, so the time the therapeutic agent-containing accessory device sits on the shelf may be kept to a minimum. These and other advantages will be readily understood from the following detailed descriptions when read in conjunction with the accompanying drawings.

BRIEF DESCRIPTION OF THE DRAWINGS

FIGS. 3A-D are schematic radial cross-sections of representative embodiments of therapeutic agent-containing sleeves.

FIG. 4A is a schematic drawing of a top view of a sleeve.

FIG. 4B is a schematic drawing of a cross-section of the sleeve in FIG. 4a taken through line 4b-4b.

FIGS. 4C-D are schematic drawings of head on back and front views of the sleeve of FIG. 4A, as viewed along lines 4c and 4d, respectively.

FIGS. 5D-E are a schematic drawings of head on front and back views of the sleeve receiving element depicted in FIG. 5c as viewed along lines 5d and 5e, respectively.

FIG. 7C is a schematic drawing of an exploded side view of the sleeve engagement element and sleeve receiving element shown in FIG. 7A.

FIG. 7D is a schematic drawing of an opposing side view (relative to FIG. 7C) of the sleeve engagement element shown in FIG. 7C.

FIG. 7E is a schematic drawing of a cross section taken along line 7e-7e of FIG. 7A.

FIG. 7F is a schematic drawing of a cross section taken along line 7f-7f of FIG. 7A.

FIG. 7G is a schematic drawing of an alternative embodiment of a cross section taken along line 7e-7e of FIG. 7A.

Figure 1A:
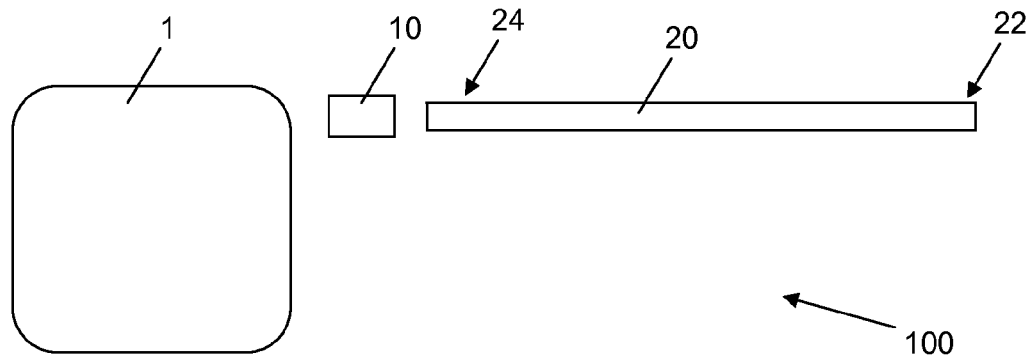
FIGS. 1A-B are schematic side views of components of a representative implantable medical device system including a therapeutic agent-containing sleeve.

The drawings are not necessarily to scale. Like numbers used in the figures refer to like components, steps, etc. However, it will be understood that the use of a number to refer to a component, step, etc. in a given figure is not intended to limit the component, step, etc. in another figure labeled with the same number. In addition, the use of different numbers to refer to components, steps, etc. is not intended to indicate that the different numbered components, steps, etc. cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used herein, an "effective amount" of an anti-infective agent is an amount that prevents, reduces the severity of, or delays an infection.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

Unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

The present disclosure describes, inter alia, a therapeutic agent-containing accessory device, such as a drug-containing polymeric sleeve, that contains a releasable therapeutic agent and that is configured to be disposed about an implantable therapy delivery element, such as a lead or catheter. The accessory device may be configured to snuggly engage the lead or catheter or may be configured to be disposed loosely about the lead or catheter. The accessory device may be placed about a proximal portion of a therapy delivery element in proximity to where the accessory device couples to an active implantable medical device, such as a neurostimulator or an infusion device. This will allow the accessory device or sleeve to release the therapeutic agent in the subcutaneous pocket into which the active device is implanted, because the sleeve is positioned near the active device. By releasing therapeutic agent in the subcutaneous implant pocket, diseases associated with the subcutaneous pocket implantation, such as infection, scarring, and pain, can be directly targeted.

Because the therapeutic agent-containing sleeve is separate from the therapy delivery element, the sleeve may be subjected to a different sterilization process from the delivery element, which may be helpful in situations where the therapeutic agent is not compatible with the sterilization process of the therapy delivery element. Further advantages of having the sleeve separate from the therapy delivery element until implantation, or just prior to implantation, include (i) the ability to package the sleeve and the delivery element separately so that the time the therapeutic agent-containing sleeve remains on the shelf can be reduced, and (ii) allowing a physician or healthcare provider to make a determination as to whether to include the therapeutic agent-containing device in the implant procedure or make a determination as to which therapeutic agent should be used with a particular implant procedure. These and other advantages will be readily understood from the following detailed descriptions when read in conjunction with the accompanying drawings.

Figure 1B:
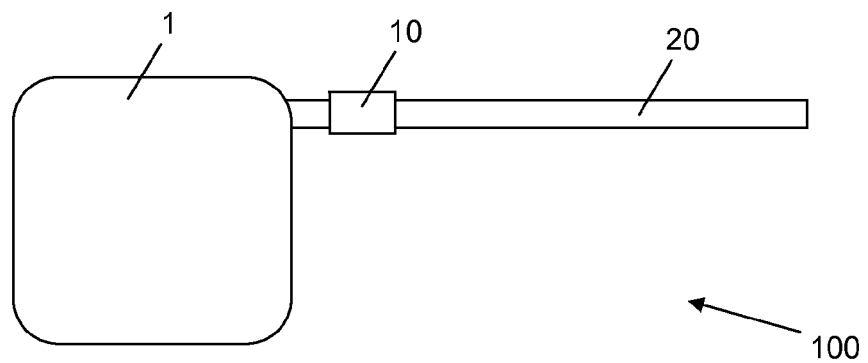

Referring to FIGS. 1A-B, a system 100 including an active implantable medical device 1, a therapy delivery element 20 operably couplable to the active device 1, and a therapeutic agent-containing sleeve 10 configured to be disposed about and snuggly engage the delivery element 20, are shown. Any active implantable medical device 1 may be included in system 100. For example, the active implantable medical device 1 may be an implantable signal generator, such as a neurostimulator, a gastric stimulator, a defibrillator, or a pacemaker; an implantable cochlear device; an implantable monitoring device; an implantable drug infusion device; or the like. Any suitable therapy delivery element 20 may be included in the system 100. For example, the therapy delivery device 20 may be a catheter or a lead; an adaptor to couple a catheter or a lead to the active device 1, such as a lead extension; or the like. In numerous embodiments, therapy delivery element 20 is an elongate element that can deliver therapy, withdraw fluid, sense a parameter, or diagnose a condition. The therapy delivery element 20 has a proximal end 24 and a distal end 22. The proximal end 24 is positioned closest to the active device 1 when the element 20 is operably coupled to the active device 1.

Figure 2:
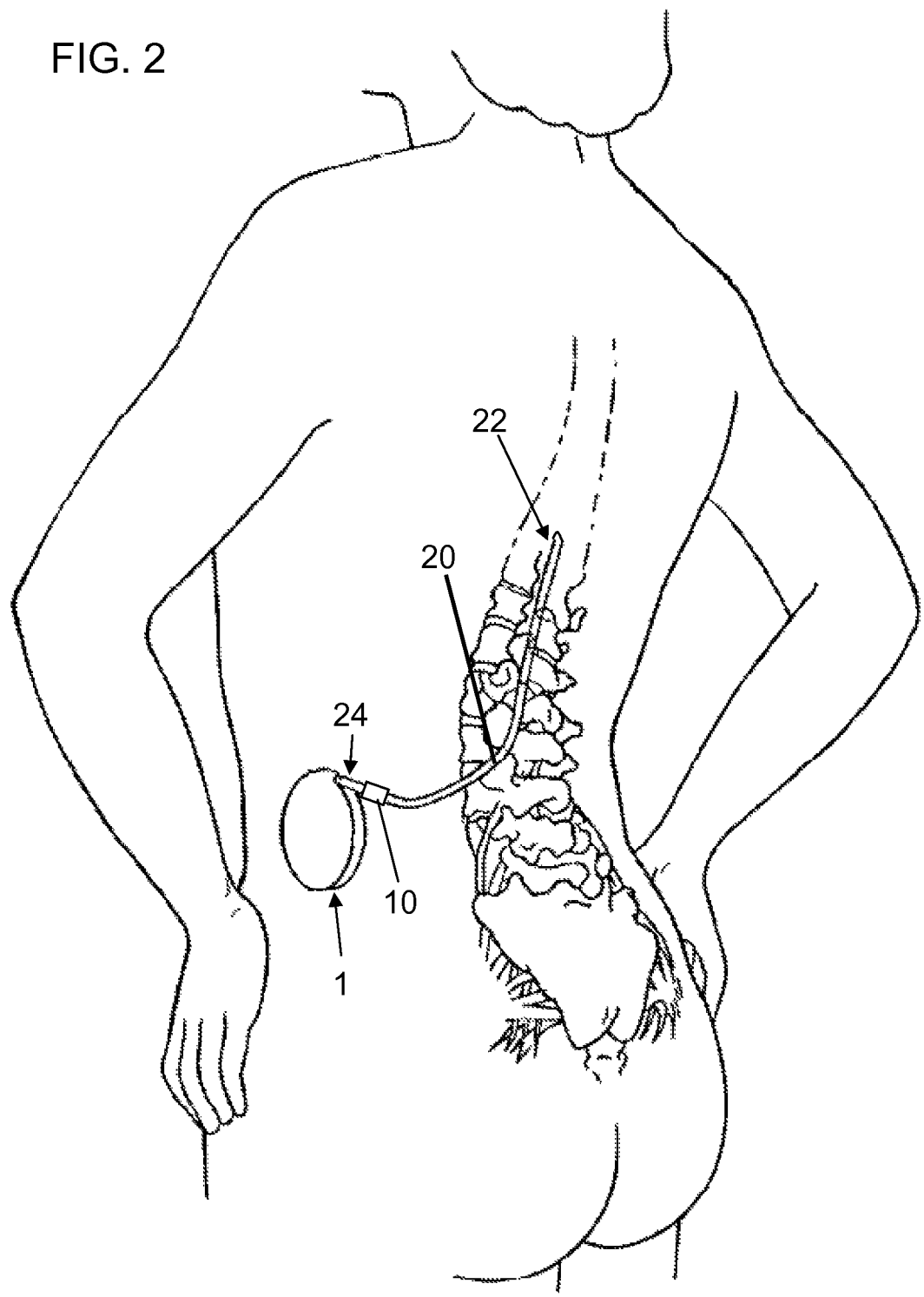
FIG. 2 is a diagrammatic representation of a representative environment of a system implanted in a patient.

Referring to FIG. 2, a general representative environment for an implanted medical system is shown. Medical device 1, in the depicted embodiment, is subcutaneously implanted in a patient in an abdominal region. Of course, device 1 may be implanted in any suitable and medically acceptable location in the patient, such as the buttocks, the pectoral region, in the skull, behind the ear, etc. A distal portion 22 of therapy delivery element 20 is positioned in the patient at a location where therapy is desired to be delivered. In the embodiment depicted, the distal portion 22 of therapy delivery element 20 is positioned within or along a spinal canal or cord of a patient. However, it will be understood that distal portion 22 of therapy delivery element 20 may be placed in any desired location to achieve its intended purpose, such as a diagnostic, monitoring, or therapeutic purpose. In the depicted embodiment, proximal end 24 of therapy delivery element 20 is coupled to medical device 1.

In many embodiments, the therapy sleeve 10 is disposed about the therapy delivery element in proximity to the proximal end 24 of the element 20; e.g. 10 centimeters or less, or 5 cm or less, from the proximal end. In various embodiments, the sleeve 10 is positioned on the element 20 such that the sleeve 10 remains in a subcutaneous pocket in which the active device 1 is implanted.

Referring to FIGS. 3A-D, schematic radial cross-sections of representative sleeves 10 are shown. Therapeutic agent 25 is associated with a body member 11 of the sleeve 10. In some embodiments, the body member 11 forms the sleeve 10. In various embodiments, at least a portion of the therapeutic agent 25 is associated with the body member 11 such that, when the sleeve 10 is contacted with a tissue or fluid of a patient, the therapeutic agent 25 releases from the body member or elutes into the tissue or fluid. Therapeutic agent 25 may be associated with body member 11 in any manner such that introduction of the sleeve 10 to a tissue of a subject allows for the therapeutic agent 25 to elute or dissolve into the tissue. FIG. 3A shows an example where therapeutic agent 25 is incorporated into the body member 11; FIG. 3B shows an example where therapeutic agent 25 is associated with an external surface of the body member 11; and FIG. 3C shows and example where therapeutic agent 25 is incorporated into body member 11 and associated with an external surface of body member 11. FIG. 3D shows an example where body member 11 includes more than one layer 11', 11". Therapeutic agent 25 is incorporated into one layer 11" but not the other 11'. Of course any other suitable arrangement of one or more therapeutic agents with one or more layers of a body member of a sleeve may be employed. As shown in FIGS. 3A-B, body member 11 forms a lumen 15. As will be described in more detail below, e.g. with regard to FIGS. 4-9, the body member 11 and lumen 15 are configured to permit the sleeve 10 to be disposed about and snuggly engage a therapy delivery element.

Body member 11 or layers 11', 11" of body member 11 may be formed from any suitable material. In various embodiments (e.g., as described below with regard to FIGS. 4-9), body member 11 or layers thereof are formed from elastic material. Examples of suitable elastic materials include copolymers of styrene-butadiene, polybutadiene, polymers formed from ethylene-propylene diene monomers, polychloroprene, polyisoprene, copolymers of acrylonitrile and butadiene, copolymers of isobutyldiene and isoprene, polyurethanes and the like. In various embodiments, body portion 11 of sleeve 10 is formed of material capable of being stretched up to about 50% or more without substantial loss of structural integrity. For example, body portion 11 may be capable of being stretched up to about 75% or more, 100% or more, 150% or more, or 200% or more. Silicone an example of an elastic material that is generally expandable up to about 100% or more without substantial loss of structural integrity.

Regardless of the material(s) from which the body 11 is formed, one or more therapeutic agents are disposed in, on, or about, generally associated with, one or more layers 11', 11" of the body member 11 of the sleeve 10 such that an effective amount of therapeutic agent 25 may be released from the body member 11 for a desired period of time. As used herein, "released" or the like, as it relates to a therapeutic agent 25 released from a sleeve 10, means being placed in a position to carry out a therapeutic effect when the sleeve 10 is implanted in a patient. For example, the therapeutic agent 25 may elute from the body member 11 into surrounding tissue or may migrate to an external surface of the body member 11 to exert an intended effect. The sleeve 10 or body member 11 may include therapeutic agent 25 at any suitable concentration. For example, therapeutic agent 25 may comprise about 0.1% to about 50%, or from about 1% to about 10%, of the weight of the body member 11 or a layer 11', 11" of a body member 11. In some circumstances, it may be desirable to place a higher concentration of therapeutic agent 25 in one or more layers relative to other layers; e.g., when continued infusion of therapeutic agent 25 into patient tissue over time is desired.

The release profile of therapeutic agent 25 from the sleeve 10 may be varied. As described above, location of therapeutic agent 25 in or on the sleeve 10, as well as concentration of therapeutic agent 25 at a location, provides a means for achieving control over when therapeutic agent 25 is released. The release profile may be varied by controlling the nature of the therapeutic agent 25 to be released. For example, agents 25 having greater molecular mass or size may elute more slowly than agents 25 having lesser molecular mass or size. Interactions between therapeutic agent 25 and components of body member 11 or layers 11', 11" of the body member 11 may also affect the rate at which therapeutic agent 25 is released from the sleeve 10. With these and other considerations in mind, it may be desirable, in some circumstances, to vary the location of slower eluting therapeutic agents 25 and faster eluting therapeutic agents 25 within or on the sleeve 10.

For example, in situations, e.g. where the sleeve 10 may be permanently implanted into a subject, it may be desirable to elute roughly the same amount of a therapeutic agent 25 over a period of time. One way to achieve substantially uniform release of two or more therapeutic agents 25 over time is to dispose a slower eluting therapeutic agent 25 near the surface of the sleeve from which the agent will elute and dispose a faster eluting therapeutic agent 25 further from the surface from which the agents will elute. Alternatively, it may be desirable to load a substantial amount of reserve therapeutic agent 25, whether slow or fast eluting, into or on sleeve 10, such that the reserve replenishes the supply of therapeutic agent 25 at or near the surface of sleeve 10 from which the agent 25 will be released. In some situations it may be desirable to load a therapeutic agent 25 in a delayed release vector, which vector is disposed in, on or about the body member or a layer of the body member, and load different therapeutic agent 25 in the body member 11 or the layer 11', 11".

The rate at which therapeutic agent may be released from the sleeve into tissue may also be controlled by properties of coating layers, vectors, or body members, as well as the manner in which therapeutic agent is disposed on or in coating layers or body members.

In various embodiments, one or more therapeutic agents are coated onto an underlying substrate of the body member of a sleeve to form a coating layer. The coating layer may be formed of any material capable of releasing the one or more therapeutic agents into tissue when placed implanted in a patient. Preferably, the coating layer is suitable for at least temporary use within a human body. The coating layer is also preferably compatible with therapeutic agent.

Examples of commonly used materials that may be used to form coating layers include polymers such as silicones, polyamines, polystyrene, polyurethane, acrylates, polysilanes, polysulfone, methoxysilanes, and the like. Other polymers that may be utilized include polyolefins, polyisobutylene and ethylene-alphaolefin copolymers; acrylic polymers and copolymers, ethylene-covinylacetate, polybutylmethacrylate; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; polycarbonates; polyoxymethylenes; polyimides; polyethers; epoxy resins; polyurethanes; rayon; rayon-triacetate; cellulose; cellulose acetate, cellulose butyrate; cellulose acetate butyrate; cellophane; cellulose nitrate; cellulose propionate; cellulose ethers; carboxymethyl cellulose; polyphenyleneoxide; and polytetrafluoroethylene (PTFE), including expanded PTFE (ePTFE).

One or more coating layer may include or be formed from a biodegradable polymeric material, such as synthetic or natural bioabsorbable polymers. Synthetic bioabsorbable polymeric materials that can be used to form the coating layers include poly(L-lactic acid), polycaprolactone, poly (lactide-co-glycolide), poly(ethylene-vinyl acetate), poly (hydroxybutyrate-covalerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly (iminocarbonate), copoly(ether-esters) such as PEO/PLA, polyalkylene oxalates, and polyphosphazenes. In various embodiments, the polymeric materials include or are formed from natural bioabsorbable polymers such as fibrin, fibrinogen, cellulose, starch, collagen, and hyaluronic acid.

Coating layers may include or be formed from polymeric materials designed to control the rate at which therapeutic agent is released from the polymeric material. Any known or developed technology may be used to control the release rate. For example, a coating layer may be designed according to the teachings of WO/04026361, entitled "Controllable Drug Releasing Gradient Coating for Medical Devices."

A coating layer of the sleeve may be in the form of a tube, sheath, sleeve, coating, or the like. A coating layer may be extruded, molded, coated on a substrate portion of a body member, grafted onto a substrate portion of a body member, embedded within a body member, adsorbed to a body member, etc. Polymers of coating layers may be porous or non-porous. Porous materials known in the art include those disclosed in U.S. Pat. No. 5,609,629 (Fearnot et al.) and U.S. Pat. No. 5,591,227 (Dinh et al.). Typically polymers are non-porous. However, non-porous polymers may be made porous through known or developed techniques, such as extruding with $CO_2$ or by foaming the polymeric material prior to extrusion or coating.

Depending upon the type of materials used to form coating layers, the coatings can be applied to the surface of a substrate portion of a body member or an underlying coating layer through any coating processes known or developed in the art. One method includes directly bonding the coating material to a surface of a substrate. By directly attaching a polymer coating to the substrate, covalent chemical bonding techniques may be utilized. The substrate surface may possess chemical functional groups on its surface such as carbonyl groups, primary amines, hydroxyl groups, or silane groups which will form strong, chemical bonds with similar groups on polymeric coating material utilized. In the absence of such chemical forming functional group, known techniques may be utilized to activate the material's surface before coupling the coating or therapeutic agent. Surface activation is a process of generating, or producing, reactive chemical functional groups using chemical or physical techniques such as, but not limited to, ionization, heating, photochemical activation, oxidizing acids, sintering, physical vapor deposition, chemical vapor deposition, and etching with strong organic solvents. Alternatively, the coating may be indirectly bound to a substrate through intermolecular attractions such as ionic or Van der Waals forces.

One or more therapeutic agents may be incorporated into a coating layer in any suitable manner. For example, the therapeutic agent can be covalently grafted to a polymer of the coating layer, either alone or with a surface graft polymer. Alternatively, therapeutic agent may be coated onto the surface of the polymer either alone or intermixed with an overcoating polymer. Therapeutic agent may be physically blended with a polymer of a coating layer as in a solid-solid solution. Therapeutic agent may be impregnated into a polymer by swelling the polymer in a solution of the appropriate solvent. Any means of incorporating therapeutic agent into or on a coating layer may be used, provided that therapeutic agent may be released, leached or diffuse from coating layer on contact with bodily fluid or tissue.

A polymer of a coating layer and a therapeutic agent may be intimately mixed either by blending or using a solvent in which they are both soluble. This mixture can then be formed into the desired shape or coated onto an underlying structure of the medical device. One exemplary method includes adding one or more therapeutic agents to a solvated polymer to form a therapeutic agent/polymer solution. The therapeutic agent/polymer solution can then be applied directly to the surface of body member; for example, by either spraying or dip coating the sleeve. As the solvent dries or evaporates, the therapeutic agent/polymer coating is deposited on delivery element. Furthermore, multiple applications can be used to ensure that the coating is generally uniform and a sufficient amount of therapeutic agent has been applied to the sleeve.

Alternatively or in addition, an overcoating polymer, which may or may not be the same polymer that forms a substrate layer of body member or an underling coating layer, and therapeutic agent are intimately mixed, either by blending or using a solvent in which they are both soluble, and coated onto body member or underling coating layer. Any overcoating polymer may be used, as long as the polymer is able to bond (either chemically or physically) to the underlying layer. Of course, a polymer layer may be swelled with an appropriate solvent, allowing a therapeutic agent to impregnate the polymer.

In some embodiments, one or more therapeutic agents are covalently grafted onto a substrate forming the body member or a layer of the body member of the sleeve. This can be done with or without a surface graft polymer. Surface grafting can be initiated by corona discharge, UV irradiation, and ionizing radiation. Alternatively, the ceric ion method, previously disclosed in U.S. Pat. No. 5,229,172 (Cahalan et al.), may be used to initiate surface grafting.

It will be understood that therapeutic agent 25, as depicted in FIGS. 3A-D or elsewhere in this disclosure, may refer to a plurality of different therapeutic agents. Any therapeutic agent(s) may be disposed in, on, or about a sleeve. Because it may be desirable to treat or prevent infection, inflammation, or diseases associated with implantation of a medical device, it may be desirable to dispose one or more anti-infective agents, one or more anti-inflammatory agents, one or more other therapeutic agents, or a combination thereof in, on, or about at least a portion of a body member 11 of a sleeve 10. In addition or alternatively, it may be desirable to deliver a local anesthetic to reduce pain associated with the implant procedure. Additional or other agents 25 that may be disposed in, on, or about sleeve 10 will be readily evident to one of skill in the art. A brief summary of some non-limiting classes of therapeutic agents 25 that may be used follows.

1. Anti-Infective Agents

Any anti-infective agent may be used in accordance with various embodiments of the invention. As used herein, "anti-infective agent" means an agent that kills or inhibits the growth of an infective organism, such as a microbe or a population of microbes. Anti-infective agents include antibiotics and antiseptics.

A. Antibiotic

Any antibiotic suitable for use in a human may be used in accordance with various embodiments disclosed herein. The antibacterial agent may have bacteriostatic and/or bacteriocidal activities. Nonlimiting examples of classes of antibiotics that may be used include tetracyclines (e.g. minocycline), rifamycins (e.g. rifampin), macrolides (e.g. erythromycin), penicillins (e.g. nafcillin), cephalosporins (e.g. cefazolin), other beta-lactam antibiotics (e.g. imipenem, aztreonam), aminoglycosides (e.g. gentamicin), chloramphenicol, sulfonamides (e.g. sulfamethoxazole), glycopeptides (e.g. vancomycin), quinolones (e.g. ciprofloxacin), fusidic acid, trimethoprim, metronidazole, clindamycin, mupirocin, polyenes (e.g. amphotericin B), azoles (e.g. fluconazole) and beta-lactam inhibitors (e.g. sulbactam). Nonlimiting examples of specific antibiotics that may be used include minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, and nystatin. Other examples of antibiotics, such as those listed in Sakamoto et al., U.S. Pat. No. 4,642,104, which is herein incorporated by reference in its entirety, may also be used. One of ordinary skill in the art will recognize other antibiotics that may be used.

In general, it is desirable that the selected antibiotic(s) kill or inhibit the growth of one or more bacteria that are associated with infection following surgical implantation of a medical device. Such bacteria are recognized by those of ordinary skill in the art and include *Staphylococcus aureus, Staphylococcus epidermis*, and *Escherichia coli*. Preferably, the antibiotic(s) selected are effective against strains of bacteria that are resistant to one or more antibiotic.

To enhance the likelihood that bacteria will be killed or inhibited, it may be desirable to combine two or more antibiotics. It may also be desirable to combine one or more antibiotic with one or more antiseptic. It will be recognized by one of ordinary skill in the art that antimicrobial agents having different mechanisms of action and/or different spectrums of action may be most effective in achieving such an effect. In an embodiment, a combination of rifampin and minocycline is used. In an embodiment, a combination of rifampin and clindamycin is used.

B. Antiseptic

Any antiseptic suitable for use in a human may be used in accordance with various embodiments. As used herein, "antiseptic" means an agent capable of killing or inhibiting the growth of one or more of bacteria, fungi, or viruses. Antiseptic includes disinfectants. Nonlimiting examples of antiseptics include hexachlorophene, cationic bisiguanides (i.e. chlorhexidine, cyclohexidine) iodine and iodophores (i.e. povidone-iodine), para-chloro-meta-xylenol, triclosan, furan medical preparations (i.e. nitrofurantoin, nitrofurazone), methenamine, aldehydes (glutaraldehyde, formaldehyde), silver-containing compounds (silver sulfadiazene, silver metal, silver ion, silver nitrate, silver acetate, silver protein, silver lactate, silver picrate, silver sulfate), and alcohols. One of ordinary skill in the art will recognize other antiseptics that may be employed in accordance with this disclosure.

It is desirable that the antiseptic(s) selected kill or inhibit the growth of one or more microbe that are associated with infection following surgical implantation of a medical device. Such microbes are recognized by those of ordinary skill in the art and include *Staphylococcus aureus, Staphylococcus epidermis, Escherichia coli, Pseudomonas aeruginosa*, and *Candida*.

To enhance the likelihood that microbes will be killed or inhibited, it may be desirable to combine two or more antiseptics. It may also be desirable to combine one or more antiseptics with one or more antibiotics. It will be recognized by one of ordinary skill in the art that antimicrobial agents having different mechanisms of action and/or different spectrums of action may be most effective in achieving such an effect. In a particular embodiment, a combination of chlorohexidine and silver sulfadiazine is used.

C. Antiviral

Any antiviral agent suitable for use in a human may be used in accordance with various embodiments. Nonlimiting examples of antiviral agents include acyclovir and acyclovir prodrugs, famcyclovir, zidovudine, didanosine, stavudine, lamivudine, zalcitabine, saquinavir, indinavir, ritonavir, n-docosanol, tromantadine and idoxuridine. One of ordinary skill in the art will recognize other antiviral agent that may be employed in accordance with this disclosure.

To enhance the likelihood that viruses will be killed or inhibited, it may be desirable to combine two or more antiviral agents. It may also be desirable to combine one or more antiseptics with one or more antiviral agent.

D. Anti-Fungal

Any anti-fungal agent suitable for use in a human may be used in accordance with various embodiments. Nonlimiting examples of anti-fungal agents include amorolfine, isoconazole, clotrimazole, econazole, miconazole, nystatin, terbinafine, bifonazole, amphotericin, griseo fulvin, ketoconazole, fluconazole and flucytosine, salicylic acid, fezatione, ticlatone, tolnaftate, triacetin, zinc, pyrithione and sodium pyrithione. One of ordinary skill in the art will recognize other anti-fungal agents that may be employed in accordance with this disclosure.

To enhance the likelihood that fungi will be killed or inhibited, it may be desirable to combine two or more anti-fungal agents. It may also be desirable to combine one or more antiseptics with one or more anti-fungal agent.

E. Elution Profile and Concentration of Anti-Infective Agents

As discussed in more detail in co-pending application Ser. No. 12/104,932, filed on Apr. 17, 2008 and published on Oct. 23, 2008 as US 2008/0260796, anti-microbial agents can be effective at preventing infection when rapidly eluted from a polymeric material placed in proximity to an implantable medical device. Accordingly, in some embodiments where one or more antimicrobial agents are associated with a sleeve as described herein, 60% or more (e.g., 70% or more, 80% or more, etc.) of anti-infective agent associated with the article to elute within 24 hours of being implanted in a patient. In some embodiments, substantially all the antimicrobial agent is eluted within 72 hours. In some embodiments, substantially all the antimicrobial agent is eluted within 24 hours. In various embodiments, a sleeve is configured to elute 40% or more of anti-infective agent associated with the sleeve within 48 hours of being implanted in a patient. In some embodiments, substantially all the antimicrobial agent is eluted within one week.

As further discussed in co-pending application Ser. No. 12/104,932, filed on Apr. 17, 2008 and published on Oct. 23, 2008 as US 2008/0260796, anti-microbial agents can be effective at preventing infection when they are included in articles having relatively small surface areas relative to the surface area of the primary implantable medical device. Accordingly, in some embodiments where one or more antimicrobial agents are associated with a sleeve as described herein, the exterior surface area of the sleeve is 30% or less, 20% or less, 10% or less, or 5% or less than the external surface area of device 50. As used herein, "surface area" is calculated on a macroscopic scale. For example, a smooth surface will be considered to have the same surface area as a rough or porous surface.

As further discussed in co-pending application Ser. No. 12/104,932, filed on Apr. 17, 2008 and published on Oct. 23, 2008 as US 2008/0260796, anti-microbial agents can be effective at preventing infection even at low concentrations. Accordingly, in some embodiments where one or more antimicrobial agents are associated with a sleeve as described herein, an anti-infective agent comprises 0.1% to 50%, 0.1% to 20%, 0.1% to 5%, 1% to 10%, etc. of the weight of the sleeve. In various embodiments, one or more anti-infective agent may be present in the article in an amount of 0.25 to 1% by weight of the article. In various embodiments, a sleeve includes between about 100-2000 micrograms of rifampin and between about 100-2000 micrograms of minocycline.

In various embodiments, at least 200 micrograms of minocycline and rifampin are capable of being eluted from the sleeve in a 24 hour time period between six and seven days, between five and six days, between four and five days, between three and four days, between two and three days, between one and two days, or within one day following implantation. Alternatively, or in addition, the sleeve may contain 300 micrograms or less of minocycline or rifampin seven, six, five, four, three, two, or one day following implantation.

In some embodiments, a sleeve contains between 1 and 500 micrograms (e.g., between 1 and 100 micrograms, between 3 and 50 micrograms or between 5 and 25 micrograms) of minocycline per square inch of the external surface area of the active implantable medical device and between 1 and 500 micrograms (e.g., between 1 and 100 micrograms, between 3 and 50 micrograms or between 5 and 25 micrograms) of rifampin per square inch of the external surface area of the active implantable medical device. In numerous embodiments where the sleeve includes an anti-infective agent other than minocycline or rifampin, the amount of the anti-infective agent associated with the sleeve is determined as follows: Multiply minimum inhibitory concentration (MIC) of the anti-infective agent against a strain of *S. aureus* in an amount per milliliter by the product of one milliliter times a number between the range of 1,500 and 50,000; i.e., (MIC) times (1 ml) times (between 1,500 and 50,000).

2. Anti-Inflammatory Agents

Any anti-inflammatory agent suitable for use in a human may be used in accordance with various embodiments. Non-limiting examples of anti-inflammatory agents include steroids, such as cortisone, hydrocortisone, prednisone, dexamethasone, methyl-prednisolone, an derivatives thereof, and non-steroidal anti-inflammatory agents (NSAIDs). Non-limiting examples of NSAIDS include ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol, ketoralac, flufenisal, salsalate, triethanolamine salicylate, aminopyrine, antipyrine, oxyphenbutazone, apazone, cintazone, flufenamic acid, clonixerl, clonixin, meclofenamic acid, flunixin, coichicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate.

3. Local Anesthetics

Any local anesthetic agent suitable for use in a human may be used in accordance with various embodiments. Non-limiting examples of local anesthetics agents include lidocaine, prilocaine, mepivacaine, benzocaine, bupivacaine, amethocaine, lignocaine, cocaine, cinchocaine, dibucaine, etidocaine, procaine, veratridine (selective c-fiber blocker) and articaine.

Any other suitable therapeutic agent or combination of therapeutic agents may be included in a sleeve as described or contemplated herein.

Referring now to FIGS. 4A-D, schematic drawings of various views of an embodiment of a sleeve 10 are shown. As shown in the top view of FIG. 4A, sleeve 10 includes a first opening 12, a second opening 14, and a body portion 11 between the first 12 and second openings 14. The body portion 11 is formed of elastomeric material. A lumen 15 (see FIG. 4B, which is a schematic of a cross section taken through line 4*b*-4*b* of the sleeve depicted in FIG. 3A) extends through the body portion 11 from the first opening 12 to the second opening 14. FIGS. 4C-D are schematics of head on back and front views from the perspective of lines 4*c* and 4*d* (as shown in FIG. 4A), respectively, providing a view of first 12 and second 14 openings.

In the embodiments depicted in FIG. 4-12, the sleeve 10 is shown without associated therapeutic agent and as a single layer body member 11 for purposes of convenience and clarity. It will be understood that body member 11 may include more than one layer and that therapeutic agent may be associated independently with each layer.

Referring now to FIG. 4B, at least a portion of body 11 is radially stretchable such that the body portion 11 has a first inner diameter (i.d. 1) (defined by the lumen 15) in a relaxed state and a second larger inner diameter (i.d. 2) in a stretched state (e.g., as described further below). As used herein, a "stretched state" of a body portion 11 means a state where body portion 11 has a larger inner diameter (defined by lumen 15) than in a relaxed state, and where the structural integrity of the body portion 11 is not compromised. A structurally uncompromised body portion 11 will generally be free of cracks or tears or will be capable of returning substantially to its relaxed state (i.e. to an inner diameter prior to radial stretching).

In various embodiments, sleeve 10 is a portion of an anchor, e.g. as described in copending application Ser. No. 12/056,547, filed on Mar. 27, 2008, and entitled "Anchor and Anchor Deployment Apparatus".

In various embodiments, the body 11 of the sleeve 10 is free of free or substantially free of slits or openings other than first 12 and second 14 openings. In such embodiments, the sleeve 10, due to the elastic nature of body member 11, may provide a uniform radially compressive force against a therapy delivery element about which the sleeve 10 is disposed. The absence of slits or other openings may allow for improved gripping by the sleeve 10 of a therapy delivery element. It will be understood that, in various embodiments, slits or other openings in body member 11 may be present (see, e.g., FIG. 13, discussed below).

A sleeve 10 as depicted in FIGS. 4A-D may be disposed about a therapy delivery element in any suitable manner, e.g. by employing a tool as described in copending application Ser. No. 12/056,547, filed on Mar. 27, 2008, and entitled "Anchor and Anchor Deployment Apparatus". For example an elastomeric sleeve may be disposed about a therapy delivery element by employing systems and methods depicted in FIGS. 5-6 of the present application.

Figure 5A:
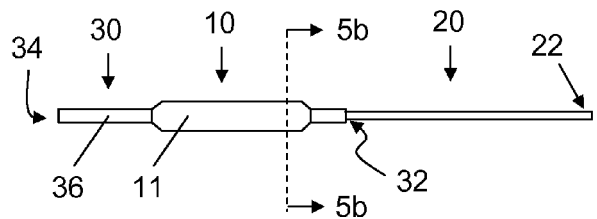
FIG. 5A is a schematic drawing of a top view of a representative system including an sleeve, sleeve receiving element, and a therapy delivery element.
Figure 5B:
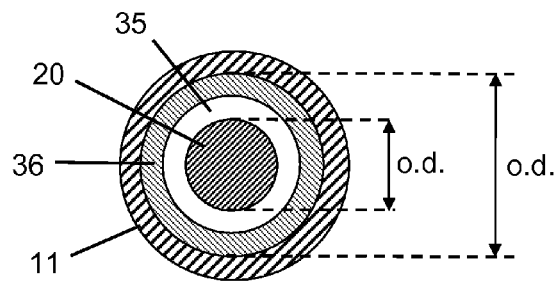
FIG. 5B is a schematic drawing of a cross section taken through line 5b-5b of FIG. 5A.
Figure 5C:
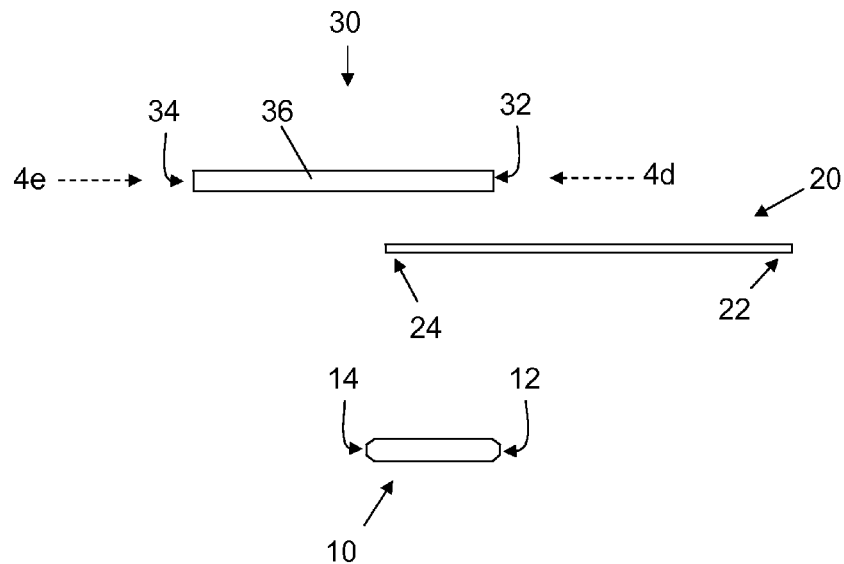
FIG. 5C is a schematic drawing of an exploded top view of the system of FIG. 5A.

Referring now to FIGS. 5A-E, schematic drawings of various views of an embodiment of a system including a sleeve 10, a therapy delivery element 20, and a sleeve receiving element 30 are shown. The sleeve receiving apparatus 30, as depicted, may serve as a sleeve deployment apparatus. FIG. 5A depicts a schematic top view of a representative system; FIG. 5B is a schematic cross section taken through line 5b-5b of FIG. 5A; FIG. 5C is a schematic exploded top view of the system depicted in FIG. 5A; and FIGS. 5D-E are schematics of head on front and back views of sleeve receiving apparatus 30 taken along lines 5d and 5e, respectively, of FIG. 5C. The sleeve receiving apparatus 30 includes an elongate member 36 and a distal opening 32. Elongate member forms a cavity or lumen 35 in communication with distal opening 32. Lumen 35 is configured to slidably receive proximal portion 24 of therapy delivery element 20. In numerous embodiments, sleeve receiving element 30 includes a proximal opening 34 and lumen 35 extends within elongate member 36 from the distal 32 to the proximal 34 opening. In such configurations, therapy delivery element 20 may be slid through lumen 35 of sleeve receiving element 30 such that proximal end 24 of therapy delivery apparatus 20 may extend beyond proximal opening 34 of sleeve receiving element 30 (not shown in FIG. 4).

As depicted in FIGS. 5A-B, sleeve 10 is disposed about sleeve receiving element 30. Body member 11 of sleeve 10 is disposed about and snuggly engages an outer surface of elongate member 36 of sleeve receiving apparatus 30. Elongate member 36 of sleeve receiving apparatus 30 has an outer diameter (o.d.) that is larger than the relaxed inner diameter (i.d. 1, see FIG. 4B) defined by lumen 15 of sleeve 10 and that is smaller than a stretched inner diameter (i.d. 2, see FIG. 4B) defined by lumen 15 of sleeve 10. As such, elastic body portion 11 of sleeve 10 may be radially stretched so that body portion 11 of sleeve 10 can be positioned about elongate member 36 of sleeve receiving element 30. The elastic properties of the material forming body member 11 of sleeve 10 allow body member 11 to snuggly engage the outer surface of elongate member 36 of the sleeve receiving element 30.

With reference to FIG. 5B, elongate body member 36 of sleeve receiving apparatus 30 defines a lumen 35. The lumen 35 is configured to slidably receive at least a portion of therapy delivery element 20. Therapy delivery element 20 has an outer diameter (o.d.) that is larger than the relaxed inner diameter (i.d. 1, see FIG. 4B) defined by lumen 15 of sleeve 10 and that is smaller than a stretched inner diameter (i.d. 2, see FIG. 4B) defined by lumen 15 of sleeve 10. It will be understood that therapy delivery element 20 is depicted in FIG. 5B as solid for purposes of illustration. If therapy delivery element 20 were a catheter, a lumen might be depicted; if therapy delivery element 20 were a lead, an insulated conductor might be depicted; etc.

Figure 6A:
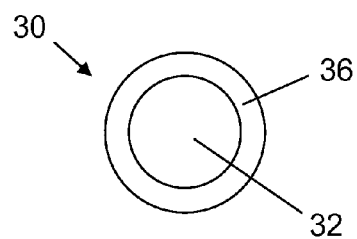
FIGS. 6A-B are schematic drawings of a representative system showing deployment of an sleeve from about a sleeve receiving element to about a therapy delivery element.
Figure 6A:
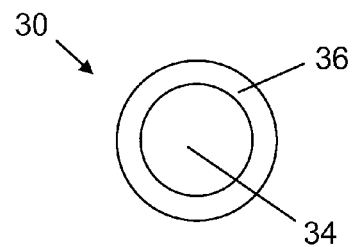
Figure 6A:
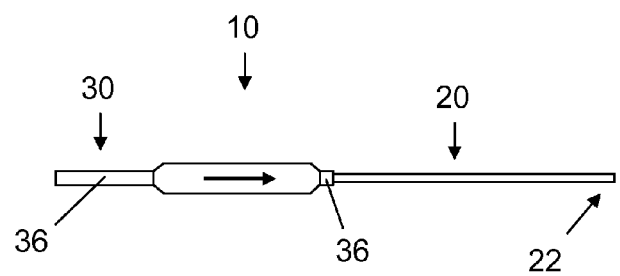
Figure 6B:
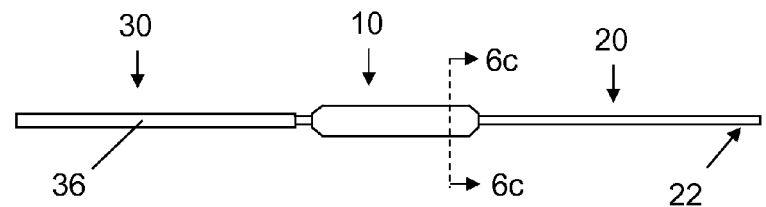
Figure 6C:
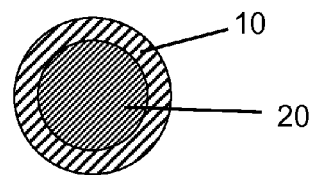
FIG. 6C is a schematic drawing of a cross section of a sleeve disposed about a therapy delivery element taken along line 6c-6c of FIG. 6B.

Referring now to FIG. 6A, which is the same top view of the system shown in FIG. 5A, except that sleeve 10 is depicted as being moved distally (in direction of arrow) along elongate body member 36 of sleeve receiving apparatus 30. Sleeve 10 is slidably moveable off distal end of elongate member 36 onto therapy delivery device 20, the proximal portion 24 of which may be disposed within lumen 35 of sleeve receiving element 30 (see, e.g., FIG. 5).

Sleeve 10 may be moved distally about elongate member 36 and onto therapy delivery element 20 through any acceptable manner, including by pushing or pulling. For example, sleeve 10 may be manually moved by a physician's fingers in some embodiments. In some embodiments, sleeve 10 is pushed with an engagement element; e.g., as discussed below with regard to FIGS. 7-9 or as described in copending application Ser. No. 12/056,547, filed on Mar. 27, 2008, and entitled "Anchor and Anchor Deployment Apparatus". When body member 11 of sleeve 10 is disposed about therapy delivery element 20, body member snuggly engages at least a portion of the outer surface of therapy delivery element 20 (see e.g., FIG. 6C), due to elastic properties of body member 11 and the larger outer diameter of therapy delivery element 20 relative to the relaxed inner diameter of body member 11 defined by lumen 15.

Preferably, sleeve body member 11 engages therapy delivery element 20 with sufficient force to prevent movement of sleeve 10 relative to therapy delivery element 20 under typical forces experienced when sleeve 10 is disposed about a therapy delivery element 20 and implanted in a patient. In various embodiments, a pull force of about 0.25 lbf (0.1 kilogram-force) or more is required to longitudinally move sleeve 10 relative to a therapy delivery element 20 that the sleeve 10 is disposed about. For example, a pull force of about 0.5 pound-force (0.2 kilogram-force), 1 pound-force (0.45 kilogram-force), 2 pound-force (0.9 kilogram-force), about 3 pound-force (1.4 kilogram-force), about 4 pound force (1.8 kilogram-force), about 5 pound-force (2.3 kilogram-force), about 6 pound-pound force (kilogram-force), or more may be required to longitudinally move sleeve 10 relative to a therapy delivery element 20. It will be understood that, in addition to the elastic properties of sleeve body member 11, other material properties of sleeve body 11 and therapy delivery element 20 may affect the pull force required to move sleeve 10 along therapy delivery element 20. For example, friction due to various interactions may play a significant role.

In many embodiments, the pull force required to move sleeve 10 about elongate member 36 of sleeve receiving element 30 is less than the pull force required to move sleeve 10 about therapy delivery element 20. This can be accomplished, despite a larger outer diameter of elongate member 36 (relative to therapy delivery element 20) by forming elongate member 36 from material that decreases frictional interaction between sleeve 10 and elongate member 36. For example, elongate member 36 may be formed of higher durometer material than therapy delivery element 20. By way of another example, elongate member 36 may be coated with a material to reduce friction, such ethylene tetrafluoroethylene (ETFE) or polytetrafluoroethylene (PTFE).

Elongate member 36 of sleeve receiving element 30 may be made of any suitable material. Preferably, elongate member 36 is formed from a rigid material, such as stainless steel, titanium, polycarbonate, polypropylene, or the like.

Figure 7A:
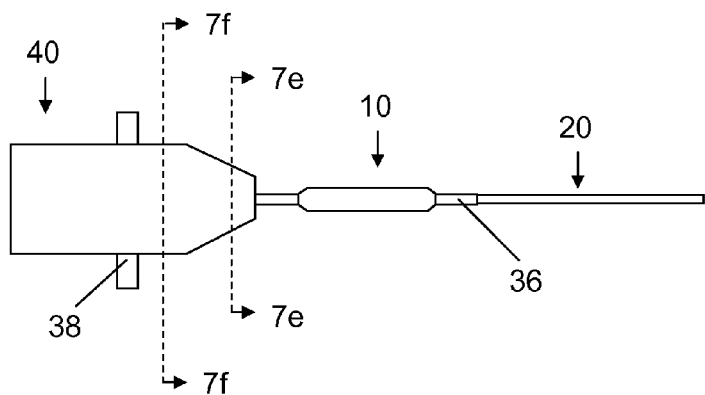
FIG. 7A is a schematic drawing of a top view of a system including a sleeve, a therapy delivery element, and a sleeve deployment apparatus that includes a sleeve receiving element and a sleeve engagement element.
Figure 7B:
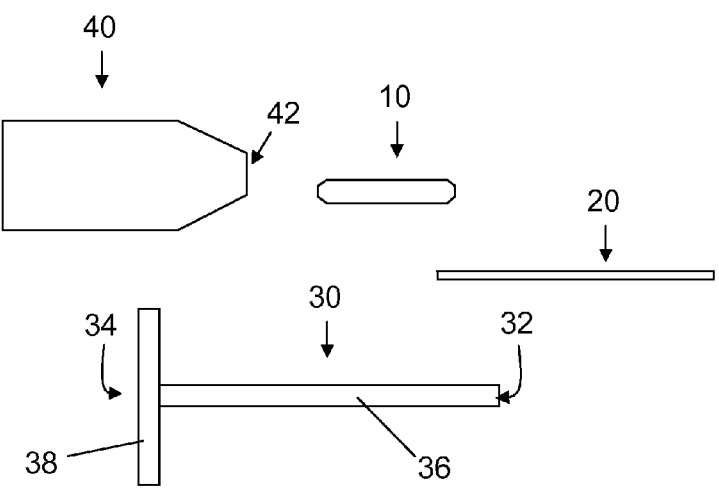
FIG. 7B is a schematic drawing of an exploded top view of the system depicted in FIG. 7A.

Referring now to FIG. 7, schematic drawings of various views of an embodiment of a system are shown. The system includes a sleeve engagement element 40 and a sleeve receiving element 30, collectively referred to as a sleeve deployment apparatus, a sleeve 10 and a therapy delivery element 20. FIG. 7A is a top view of the system; FIG. 7B is an exploded top view of the system depicted in FIG. 7A; FIG. 7C is an exploded side view of an embodiment of a sleeve engagement element 40 and sleeve receiving element 30 depicted in FIG. 7A; FIG. 7D is an opposing side view (relative to FIG. 7C) of sleeve engagement element 40; FIG. 7E is a cross section taken along line 7e-7e of FIG. 7A, FIG. 7F is a cross section taken along line 7f-7f of FIG. 7A; and FIG. 7G is a an alternative embodiment (relative to FIG. 7E) of a cross section taken along line 7e-7e of FIG. 7A. In the embodiment depicted in FIGS. 7A-C, sleeve receiving element 30 includes a handle 38 at proximal end of elongate member 36. Handle 38 is positioned generally perpendicular to the longitudinal axis of elongate member 36. The sleeve receiving element 30 including handle 38 may contain a proximal opening 34 such that lumen 35 extends within elongate member 36 from proximal opening 34 to distal opening 32. Handle 38 may be made from the same or different material than elongate body 36.

Referring to FIGS. 7C-F, sleeve engagement element 40 has a proximal opening 42. In proximity to or adjacent to the opening 42, the engagement element 40 contains a sleeve engagement feature 41. The proximal opening 42 is in communication with a channel 45 formed within the body of the element 40. The channel 45 runs generally longitudinally within at least a proximal portion of engagement element 40. Channel 45 is configured such that at least a distal portion of elongate member 36 of sleeve receiving element 30 may be slidably disposed within channel 45. In the depicted embodiment, a larger second channel 46 is formed within engagement element 40. The second channel 46 is in communication with and an extension of the first channel 45. On a side of engagement element 40 generally opposing the opening of the second channel 45, a slot 48 is formed within the body of the element 48. The slot 48 and the second channel 46 form an uninterrupted passageway through the engagement element 40. The passageway formed by the slot 48 and second channel 46 is configured such that handle 38 of sleeve receiving element 30 is slidably disposable within the passageway. When sleeve receiving element 30 is slidably disposed with sleeve engagement element 40, a portion of either side of handle 38 of receiving element 30 extends beyond the body of engagement element 40.

Referring to the alternative embodiments depicted in FIG. 7G, channel 45 may be tapered inwardly to facilitate insertion of elongate member 36 of receiving element 30 into channel 45. In the embodiments depicted in FIGS. 7C, 7E and 7G, engagement feature 41 defines channel 45 and defines opening 42. The radial dimensions of the channel 45 may be larger or substantially the same as the outer diameter of the elongate member 36.

Figure 8A:
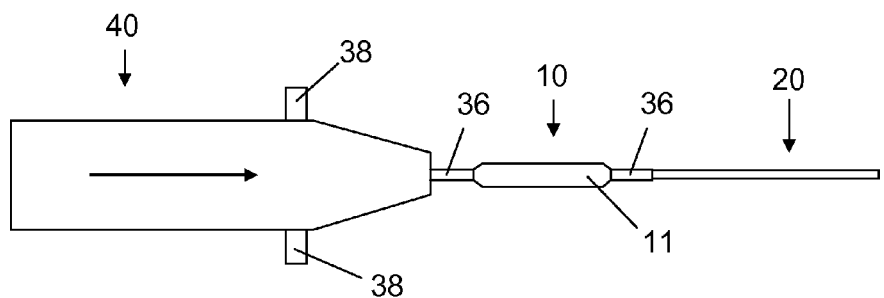
FIGS. 8A-C are schematic diagrams of top views of a system showing a sleeve engagement element employed to move a sleeve along an sleeve receiving element and onto and about a therapy delivery element.
Figure 8B:
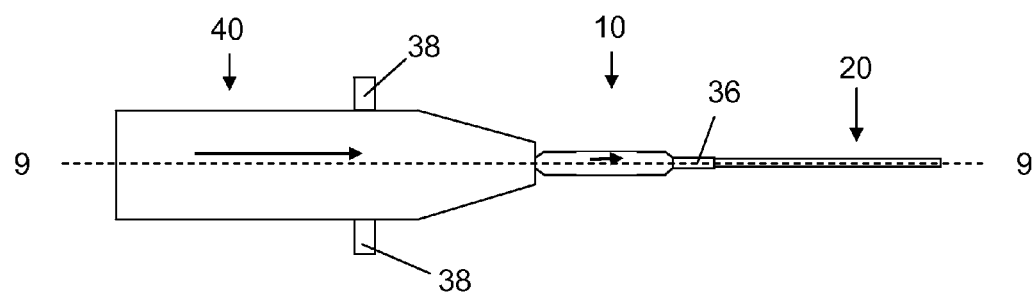
Figure 8C:
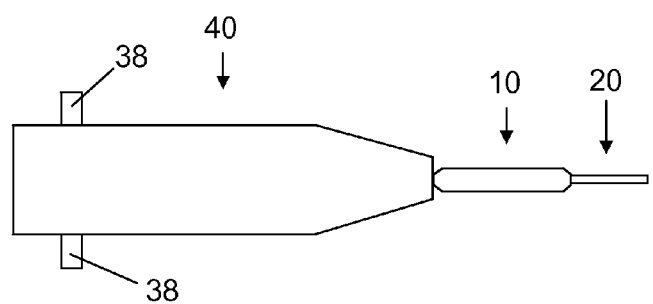

Referring to FIG. 8, sleeve engagement element 40 may be moved distally relative to sleeve receiving element 30 (see FIG. 8A) such that engagement element 40 may force an sleeve 10 disposed about elongate body 36 of receiving element 30 to move distally along the elongate body 36 (see FIG. 8B). Continued movement of engagement element 40 distally relative to sleeve receiving element 30 results in sleeve 10 being transferred about therapy delivery element 20 (see FIG. 8C). Sleeve engagement element 40 may be moved distally relative to sleeve receiving element 30 by pushing engagement element 40 relative to receiving element 30 or by pulling protruding portions of handle 38 relative to engagement element 40.

Figure 9:
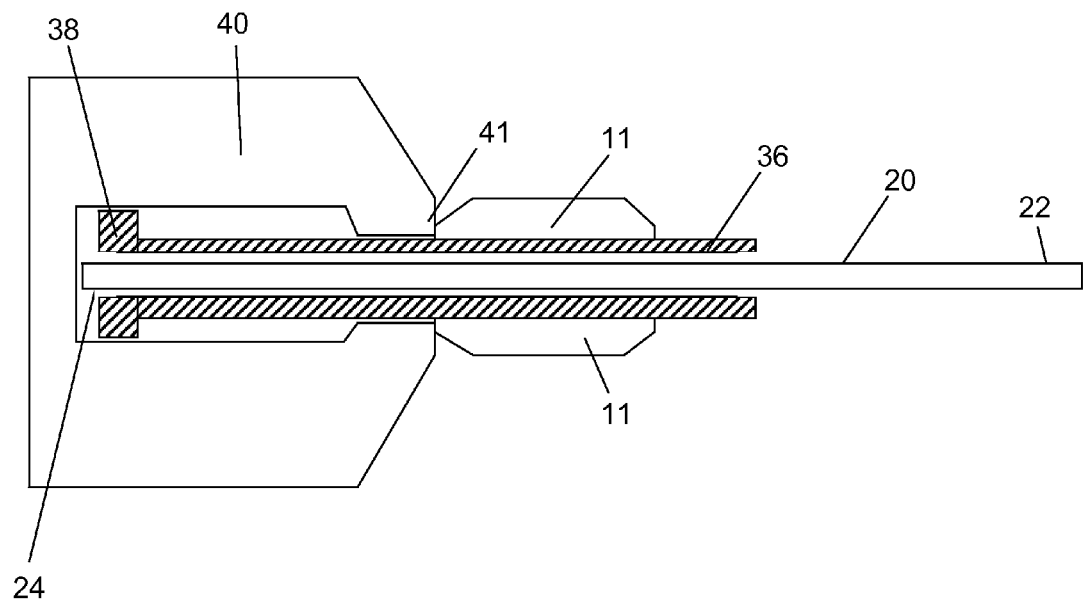
FIG. 9 is a schematic drawing of a side view of a longitudinal section taken along line 9-9 of FIG. 8B.

Referring to FIG. 9, which is schematic of a side view of a longitudinal section taken along line 9-9 of FIG. 8B, sleeve engagement element 40 is shown in contact with sleeve 10. Engagement feature 41 of engagement element 40 is configured to interact with at least a portion of sleeve 10 such that engagement feature 41 is capable of moving sleeve 10 distally along elongate member 36 of sleeve receiving element 30 when engagement element is moved distally relative to elongate member 36 of sleeve receiving element 30. In the embodiment depicted in FIG. 9, and as discussed above with regard to FIGS. 7C, 7E and 7G, engagement feature 41 defines channel 45 and proximal opening 42 of engagement element 40. The opening 42 defined by engagement feature 41, in the depicted embodiments, has dimensions that are smaller than at least a portion of the outer diameter of the body member 11 of the sleeve 10.

The sleeve deployment tools depicted in FIGS. 7-9 allows for kits having multiple sleeve receiving elements 30 with preloaded sleeve 10 to be provided with a single sleeve engagement element 40. A sleeve receiving element 30 may readily be inserted and withdrawn from engagement element 40, allowing for re-insertion of the same or another sleeve receiving element 30. However, embodiments where sleeve receiving element 30 is not removable and reinsertable into sleeve engagement element 40 are envisioned.

Sleeve engagement element 40 may be formed from any suitable material. Preferably the body of engagement element 40 is formed from a rigid material, such as stainless steel, titanium, polycarbonate, polypropylene, or the like. In various embodiments, the body of engagement element 40 is formed of a polymer having a durometer of about 75D or higher. In various embodiments, engagement element 40 is molded in its entirety.

Figure 10:
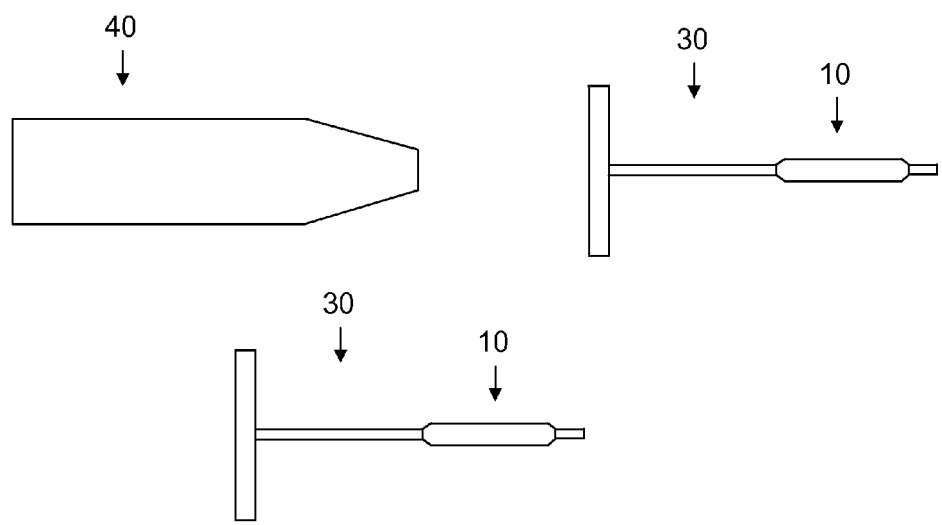
FIG. 10 is a schematic drawing of a top view of components of a kit.

Referring to FIG. 10, a schematic drawing of a top view of representative components of a kit is shown. A kit may include a sleeve engagement element 40, a sleeve 10, and a sleeve receiving element 30. The sleeve 30 may be preloaded on the sleeve receiving element 30. In various embodiments, a kit includes two or more sleeve receiving elements 30 with preloaded sleeve 10. In the depicted embodiment, the sleeve receiving elements 30 are insertable, removable and reinsertable in the sleeve engagement element 40. A sleeve receiving element 30 may be preloaded in sleeve engagement element 40. A kit may further include a therapy delivery element (not shown in FIG. 11). Such kits may contain multiple sleeves, each having a different therapeutic agent, combination of agents, concentration of agent(s), etc. This will allow a physician or health care provider to select the appropriate therapeutic agent, combination of agents, concentration of agents, etc. for each procedure and patient.

Figure 11A:
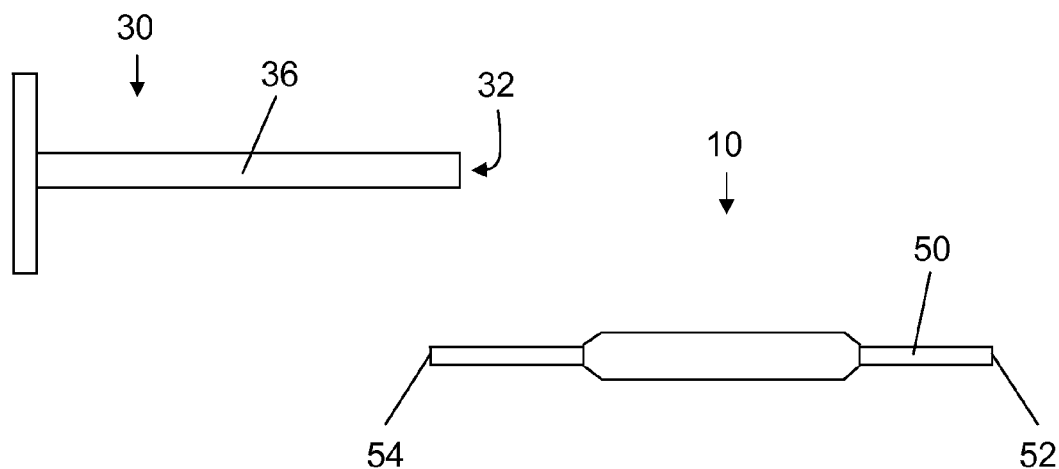
FIGS. 11A-B are schematic drawings of top views of a system including a sleeve, an insertion element, and a sleeve receiving element.
Figure 11B:
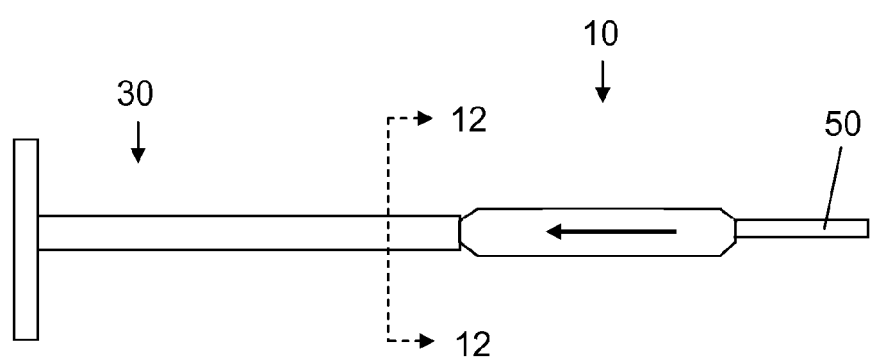
Figure 11C:
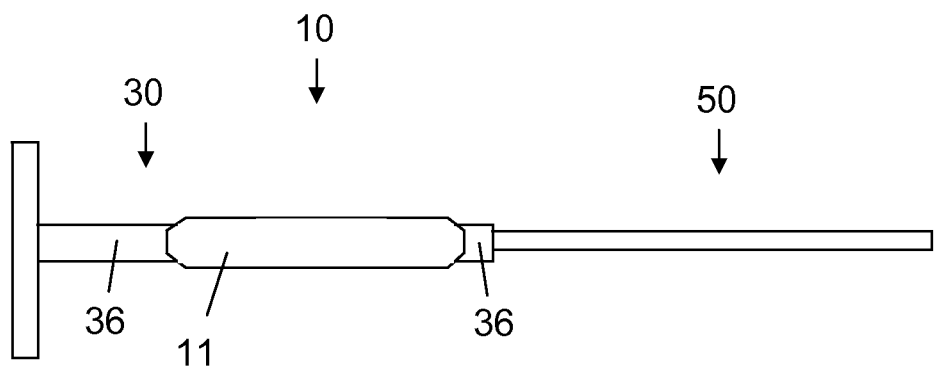
FIG. 11C is a schematic radial cross section of a system including a sleeve, an insertion element, and a sleeve receiving element.
Figure 12:
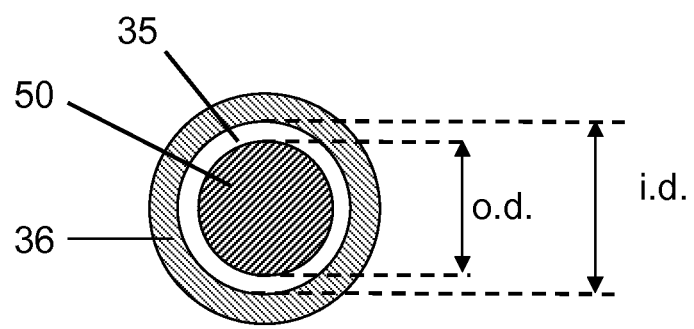
FIG. 12 is a cross section of a sleeve disposed about an insertion element taken along line 12-12 of FIG. 11.

Sleeve 10 may be loaded on sleeve receiving element 30 in any manner that retains the elastic and therapy delivery element-retaining properties of the sleeve. One suitable manner for placing sleeve 10 about sleeve receiving element 30 is shown in FIGS. 11A-C. As shown in FIG. 11A, sleeve 10 may be placed about an insertion element 50 having proximal 54 and distal 52 ends. A handle (not shown) may be attached to or form a part of a distal portion of insertion element 50. Proximal end 54 of insertion element 50 may be inserted into a lumen of sleeve receiving element 30 via proximal opening 32 (see FIG. 11B), and sleeve 10 may be moved proximally along insertion element 50 and about receiving element 30 until sleeve 10 is entirely disposed about elongate member 36 of receiving element 30 (FIG. 11C). As shown in FIG. 12, which is schematic cross section taken through line 12-12 of FIG. 1B, insertion element 50 has an outer diameter (o.d.). The outer diameter (o.d.) is larger than the relaxed inner diameter of sleeve body 11 and smaller than a radially stretched inner diameter of sleeve body 11 (see FIG. 3B). The outer diameter (o.d.) of insertion element 50 is sized to cause some radial expansion of sleeve body 11 when sleeve 10 is disposed about insertion element 50, but preferably not too much to prevent sliding of sleeve 10 about insertion element 50. Insertion element 50 outer diameter (o.d.) is preferably only slightly smaller than the inner diameter (i.d.) of elongate body 36 of receiving member 30 so that when sleeve 10 is transferred, via sliding, from insertion element 50 to receiving element 30, lumen 15 extending through sleeve body 11 (see FIG. 4B) does not undergo substantial radial expansion, as substantial radial expansion of sleeve body 11 may make it difficult to transfer sleeve 10 due to the elastic properties of sleeve body 11.

Insertion element 50 is preferably formed from a rigid material, such as stainless steel, titanium, polycarbonate, polypropylene, or the like. In various embodiments, insertion element 50 is formed of a polymer material having a durometer of about 75D or higher.

A sleeve as described herein may be of any suitable dimensions. In various embodiments, the sleeve has a length between about 0.25 inches (0.6 centimeters) and about 5 inches (13 centimeters). In some embodiments, the sleeve has an average thickness of between about 0.005 inches (0.1 centimeters) and about 0.1 inches (0.25 centimeters).

Figure 13:
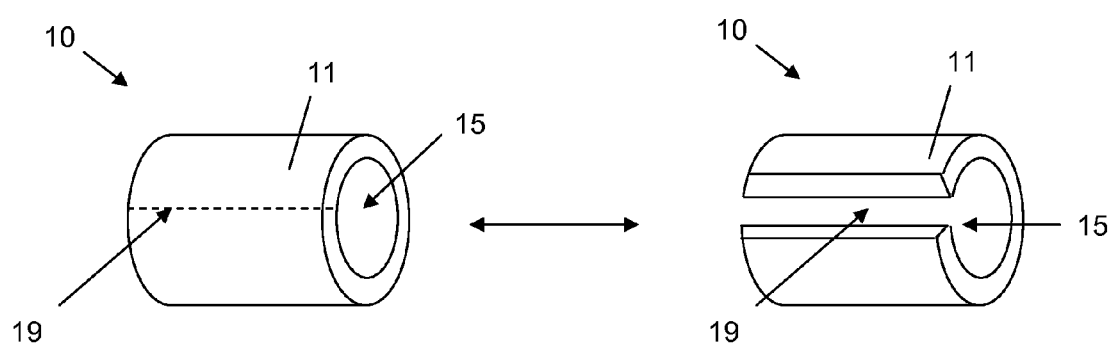
FIG. 13 shows schematic perspective views of a sleeve having a longitudinal slit.

Referring now to FIG. 13, an alternative embodiment of a therapeutic agent eluting sleeve 10 is shown. The sleeve includes a body member 11 defining a lumen 15. A longitudinal slit 19 extends the length of the body member 11. The sleeve 10 is configured such that the slit 19 may be widened sufficiently to receive a lead or catheter so that the sleeve 10 may be placed about the catheter or lead. It may be desirable to employ sleeves 10 having such slits 19 when the sleeve 10 is to be placed about a lead or catheter after the lead or catheter is connected to an active device, such as an electrical signal generator or an infusion device. The sleeve 10 may be place about a lead or catheter in any suitable manner. For example, the slit may be widened manually or a deployment tool as described above may be suitably adapted to deploy such sleeves 10 when the lead or catheter is coupled to an active device. By way of example, a deployment tool, or appropriate components thereof, may be modified to include longitudinal slits to allow for insertion of catheters or leads that are connected to an active device.

Preferably, a sleeve 10 having a slit 19 is made of a resilient material that allows the slit to return to a substantially closed form after being widened and after insertion of the lead or catheter. The resilient nature of the material will serve to retain the sleeve 10 about a lead or catheter. The resilient nature of the sleeve 10 may allow for the sleeve 10 to grippingly engage a lead or catheter. Alternatively, the sleeve 10 may loosely engage the lead or catheter.

Sleeves 10 with slits 19 may be made of any suitable material, such as the polymeric materials described above.

Thus, embodiments of the THERAPEUTIC SLEEVE FOR IMPLANTABLE MEDICAL DEVICE are disclosed. One skilled in the art will appreciate that the present invention can be practiced with embodiments other than those disclosed. The disclosed embodiments are presented for purposes of illustration and not limitation.

What is claimed is:

1. A therapeutic sleeve disposable about a therapy delivery element, the therapy delivery element having an outer diameter and an outer surface about which the sleeve is disposable, the sleeve comprising:
   a first opening;
   a second opening;
   a body member disposed between the first and second opening, the body member being formed from elastic material;
   a lumen extending though the body member from the first opening to the second opening, the lumen being configured to be disposed about at least a portion of the outer surface of the therapy delivery element; and
   a therapeutic agent releasable from the body member when implanted in a patient,
   wherein at least a portion of the body member has a first inner diameter defined by the lumen in a relaxed state and a second inner diameter defined by the lumen in a radially stretched state,
   wherein the first inner diameter is smaller than the second inner diameter, and
   wherein the first inner diameter is smaller than the outer diameter of the therapy delivery element, and the second inner diameter is larger than the outer diameter of the therapy delivery element,
   wherein the therapeutic agent is an antimicrobial agent and wherein the sleeve is configured to elute substantially all of the antimicrobial agent within one week of being implanted in a patient.

2. The sleeve of claim 1, wherein the body member is configured to grippingly engage the least a portion of the outer surface of the therapy delivery element such that a pull force of 0.25 pound-force or more is required to move the sleeve along the outer surface of the therapy delivery element.

3. The sleeve of claim 1, wherein the body member is formed of silicone.

4. The sleeve of claim 1, wherein the body member is free of slits.

5. The sleeve of claim 1, wherein the therapeutic agent is minocycline.

6. The sleeve of claim 5, wherein the sleeve further comprises rifampin, wherein the rifampin is releasable from the body member when implanted in the patient.

7. The sleeve of claim 6, wherein the therapy delivery element is operably couplable to an active implantable medical device having an exterior surface area.

8. The sleeve of claim 7, wherein the minocycline is included in the sleeve in an amount of between 3 and 50 micrograms per square inch of the exterior surface area of the active device, and wherein the rifampin is included in the sleeve in an amount between 3 and 50 micrograms per square inch of the exterior surface area of the active device.

9. The sleeve of claim 8, wherein the minocycline is present in an amount between 5 and 25 micrograms per square inch of the exterior surface area of the active device, and wherein the rifampin is present in an amount between 5 and 25 micrograms per square inch of the exterior surface area of the active device.

10. The sleeve of claim 6, wherein the sleeve includes an effective amount of minocycline and rifampin, and wherein the sleeve is configured to elute 40% or more of the minocycline and rifampin within 48 hours of being implanted in a patient.

11. The sleeve of claim 10, wherein the sleeve is configured to elute 60% or more of the minocycline and rifampin within 24 hours of being implanted in a patient.

12. The sleeve of claim 10, wherein the sleeve is configured to release substantially all the minocycline within 24 hours of being implanted.

13. The sleeve of claim 12, wherein the sleeve is configured to release substantially all the rifampin within 72 hours of being implanted.

14. A system comprising a therapeutic sleeve according to claim 1 and the therapy delivery element about which the sleeve is configured to be disposed.

15. A kit comprising:
a sleeve having a first opening, a second opening, a body member disposed between the first and second opening, and a lumen extending though the body member from the first opening to the second opening, wherein the body member is formed from an elastic material and wherein at least a portion of the body member has a first inner diameter defined by the lumen in a relaxed state and a second inner diameter defined by the lumen in a radially stretched state, wherein the first inner diameter is smaller than the second inner diameter, wherein the sleeve further includes a therapeutic agent releasable from the body member when implanted in a patient wherein the therapeutic agent is an antimicrobial agent and wherein the sleeve is configured to elute substantially all of the antimicrobial agent within one week of being implanted in a patient;
a therapy delivery element having an outer diameter and an outer surface about which the sleeve is disposable, the outer diameter being larger than the first inner diameter of the at least a portion of the body member of the sleeve and smaller than the second inner diameter of the at least a portion of the body member of the sleeve; and
a deployment apparatus including a sleeve receiving element,
the sleeve receiving element comprising an elongate member having a distal opening and a lumen extending proximally in the elongate member from the distal opening,
wherein the lumen of the elongate member is configured to slidably receive at least a portion of the therapy delivery element,
wherein the elongate member has an outer diameter larger than the first inner diameter of the at least a portion of the body member of the sleeve and smaller than the second inner diameter of the at least a portion of the body member of the sleeve such that the sleeve is disposable about the elongate member and, when the sleeve is disposed about the elongate member, the at least a portion of the body member of the sleeve engages at least a portion of the elongate member, and wherein the sleeve is moveable about the elongate member.

16. A kit for disposing a sleeve about a therapy delivery element, the therapy delivery element having an outer diameter and an outer surface about which the sleeve is disposable, the kit comprising:
the sleeve having a first opening, a second opening, a body member disposed between the first and second opening, and a lumen extending though the body member from the first opening to the second opening, wherein the body member is formed from an elastic material and wherein at least a portion of the body member has a first inner diameter defined by the lumen in a relaxed state and a second inner diameter defined by the lumen in a radially stretched state, wherein the first inner diameter is smaller than the second inner diameter, wherein the sleeve further includes a therapeutic agent releasable from the body member when implanted in a patient and wherein the outer diameter of the therapy delivery element is larger than the first inner diameter of the at least a portion of the body member of the sleeve and is smaller than the second inner diameter of the at least a portion of the body member of the sleeve wherein the therapeutic agent is an antimicrobial agent and wherein the sleeve is configured to elute substantially all of the antimicrobial agent within one week of being implanted in a patient;
a deployment apparatus including an sleeve receiving element,
the sleeve receiving element comprising an elongate member having a distal opening and a lumen extending proximally in the elongate member from the distal opening,
wherein the lumen of the elongate member is configured to slidably receive at least a portion of the therapy delivery element,
wherein the elongate member has an outer diameter larger than the first inner diameter of the at least a portion of the body member defined by the lumen of the sleeve and smaller than the second inner diameter of the at least a portion of the body member defined by lumen of the sleeve such that the sleeve is disposable about the elongate member and, when the sleeve is disposed about the elongate member, the at least a portion of the body member of the sleeve engages at least a portion of the elongate member, and wherein the sleeve is moveable about the elongate member.

17. The kit of claim 15, wherein the sleeve comprises a biodegradable polymer.

18. The kit of claim 16, wherein the sleeve comprises a biodegradable polymer.

19. The sleeve of claim 1, wherein the body member comprises a biodegradable polymer.

* * * * *